United States Patent [19]

Cianci

[11] 4,328,828

[45] May 11, 1982

[54] DRAINAGE SYSTEM WITH VENT

[75] Inventor: James P. Cianci, Cary, Ill.

[73] Assignee: The Kendall Company, Boston, Mass.

[21] Appl. No.: 187,909

[22] Filed: Sep. 17, 1980

[51] Int. Cl.³ .......................... F16K 31/00; A61J 1/00;
A61M 27/00
[52] U.S. Cl. ................................... 137/549; 251/339;
128/768; 128/272; 128/350 R
[58] Field of Search ........... 128/349 B, 349 R, 350 R,
128/768, 272; 137/549, 859, 860; 251/331, 339

[56] References Cited

U.S. PATENT DOCUMENTS

| 3,192,949 | 7/1965 | De See | 251/339 |
| 3,419,009 | 12/1968 | Ericson | 128/349 R |
| 3,463,542 | 8/1969 | Nilsen et al. | 251/339 |
| 3,599,620 | 8/1971 | Balin | 128/349 B |
| 4,066,070 | 1/1978 | Utsuzi | 128/349 B X |
| 4,070,004 | 1/1978 | Friswell | 251/331 |
| 4,116,227 | 9/1978 | Eisenberg et al. | 128/768 |
| 4,126,558 | 11/1978 | Luceyk | 137/549 X |

Primary Examiner—A. Michael Chambers
Attorney, Agent, or Firm—Powell L. Sprunger

[57] ABSTRACT

A vent for a liquid drainage system comprising, a conduit having a lumen for drainage of liquid, and a filter pervious to air and substantially impervious to the passage of bacteria, with the filter communicating with the atmosphere. The vent has a valve assembly communicating between the lumen and the filter, with the valve assembly being movable between a first closed position to prevent passage of liquid from the lumen against the filter, and a second open position to permit passage of air between the atmosphere and the lumen through the filter.

10 Claims, 6 Drawing Figures

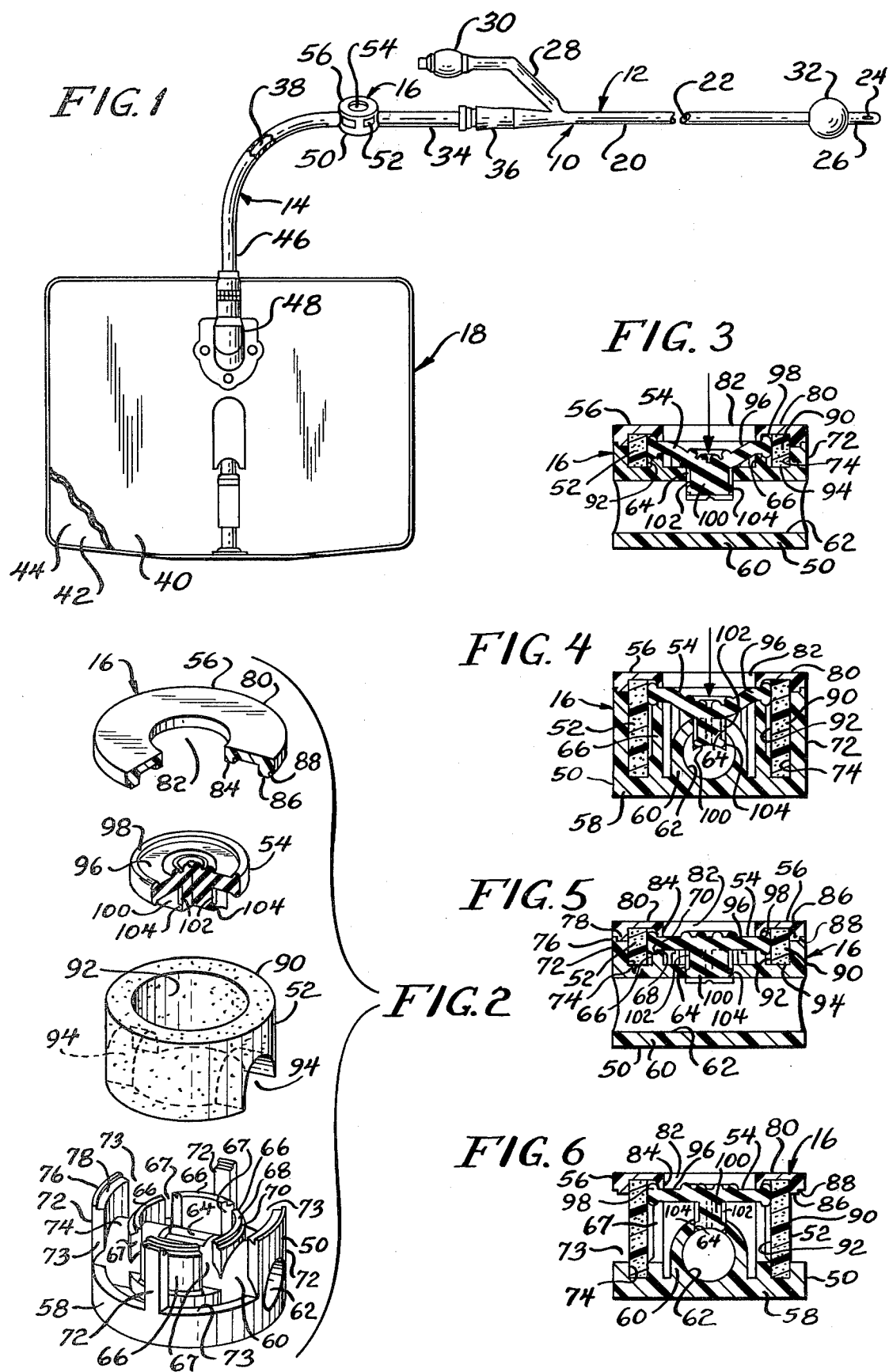

DRAINAGE SYSTEM WITH VENT

BACKGROUND OF THE INVENTION

The present invention relates to liquid drainage systems.

During catheterization of a patient, a distal end of a catheter is passed through the urethra until a drainage eye in the distal end of the catheter is located in the patient's bladder. An upstream end of a drainage tube is connected to a proximal end of the catheter located outside the patient's body, and a downstream end of the drainage tube communicates with a collection receptacle. Thus, urine from the bladder drains through the catheter drainage eye, a lumen in the catheter, and through a lumen in the drainage tube to the receptacle for collection therein.

During drainage, solid columns of urine form in the drainage tube which create a negative pressure in the drainage tube. In order to drain the urine, air must rise through the column of urine to the top of the column which is frequently a relatively slow process. Hence, the urine columns are often found in the drainage tube, and are undesirable for a number of reasons. First, the pooled urine in the drainage tube provides an easy pathway for the migration of bacteria up the drainage tube toward the patient's bladder. Second, the volume of urine in the collection receptacle is often measured by hospital personnel, and the measured volume does not include the urine located in the drainage tube resulting in an inaccurate measurement. Third, the negative pressure created by the urine columns may cause lesions in the patient's bladder.

It is possible to provide a vent for the drainage tube in order to permit passage of air from the atmosphere to the lumen of the drainage tube, thus alleviating the negative pressure in the drainage tube and causing rapid drainage through the drainage tube. Of course, it is necessary to provide a filter for such a vent in order to remove bacteria from the air which passes into the drainage tube, since the closed drainage system would otherwise become contaminated. However, it has been found that repeated contact of urine against the filter causes the filter to close, thus rendering the vent inoperable and again causing formation of urine columns and a negative pressure in the drainage tube.

SUMMARY OF THE INVENTION

The principal feature of the present invention is the provision of improved vent means for a liquid drainage system.

The drainage system has a conduit having a lumen for drainage of liquid, and the vent means has a filter pervious to air and substantially impervious to the passage of bacteria, with the filter communicating with the atmosphere. The vent means has valve means communicating between the lumen and the filter.

A feature of the present invention is that the valve means is normally closed to prevent contact of urine from the lumen against the filter.

Thus, another feature of the invention is that the valve means prevents damage to the filter by the urine during use of the device.

Yet another feature of the invention is that the valve means may be selectively opened to permit passage of air between the atmosphere and the lumen through the filter.

Accordingly, a feature of the present invention is that a negative pressure may be alleviated in the drainage lumen by actuation of the valve means.

Further features will become more fully apparent in the following description of the embodiments of this invention and from the appended claims.

DESCRIPTION OF THE DRAWINGS

In the drawings:

FIG. 1 is a fragmentary front plan view, partly broken away, of a liquid drainage system having vent means of the present invention;

FIG. 2 is an exploded view, taken partly in section, of the vent means of FIG. 1;

FIG. 3 is a sectional view of the vent means with valve means of the vent means in an open configuration;

FIG. 4 is another sectional view of the vent means with the valve means in an open configuration;

FIG. 5 is a sectional view of the vent means with the valve means in a closed configuration; and FIG. 6 is another sectional view of the vent means with the valve means in a closed configuration.

DESCRIPTION OF THE PREFERRED EMBODIMENTS

Referring now to FIG. 1, there is shown a liquid drainage system generally designated 10 comprising a catheter 12, a drainage tube 14, a vent 16 for the drainage tube 14, and a collection bag 18. The catheter 12 has an elongated shaft 20 defining a drainage lumen 22 in the shaft 20, and a drainage eye 24 in a distal end 26 of the catheter 12, with the drainage eye 24 communicating with the drainage lumen 22. The catheter 12 has an inflation lumen (not shown) extending through a side arm 28 and through the shaft 20, such that the inflation lumen communicates between valve means 30 on the side arm 28 and an inflatable retention balloon 32 adjacent the distal end 26 of the shaft 20. An upstream end 34 of the drainage tube 14 is connected to a proximal end 36 of the catheter 12, such that a lumen 38 in the drainage tube 14 communicates with the lumen 22 in the catheter 12. The collection bag 18 has a front wall 40 and a rear wall 42 which are joined together around their periphery to define a chamber 44 between the front and rear walls 40 and 42. A downstream end 46 of the drainage tube 14 is connected to the collection bag 18 by a connector 48, with the lumen 38 in the drainage tube 14 communicating with the chamber 44 through the connector 48. As will be discussed below, the vent 16 is attached to the drainage tube 14 adjacent the upstream end 34 of the drainage tube 14.

In use of the drainage system 10, the distal end 26 of the catheter 12 is passed through the urethra of a patient with the balloon 32 in an uninflated configuration until the drainage eye 24 and the retention balloon 32 are located in the patient's bladder. The upstream end 34 of the drainage tube 14 is connected to the proximal end 36 of the catheter 12 which is located outside the patient's body. Next, the retention balloon 32 is inflated by actuating the valve means 30, and pumping a fluid through the valve means 30 and inflation lumen into the retention balloon 32, such that the inflated retention balloon 32 retains the catheter in the patient's body. During catheterization, urine drains through the drainage eye 24, the drainage lumen 22 of the catheter 12, the lumen 38 of the drainage tube 14, and through the connector 48 into the chamber 44 for retention in the collection bag 18. However, during drainage of liquid, it has been found that columns of liquid form in the lumen 38 of the drainage tube 14, which impedes liquid drainage and which create an undesired negative pressure in the drainage system 10. In order to alleviate the negative pressure and permit rapid drainage in the drainage tube 14, the vent 16 is provided to permit passage of air from the atmosphere into the drainage lumen 38, as will be further discussed below.

With reference to FIGS. 2, 5, and 6, the vent 16 comprises a housing 50, a filter 52, and an elastic valve element 54, with the housing 50 having an annular cap 56. The housing 50 has a base 58, and an elongated conduit section 60 in a central portion of the base 58 and defining a lumen 62. The conduit section 60 has a generally rectangular opening 64 extending through the conduit section 60 and communicating with the lumen 62. With reference to FIG. 1, opposed ends in the upstream portion 34 of the drainage tube 14 are connected to the housing 50, with the lumen 38 of the drainage tube 14 communicating with the lumen 62 of the conduit section 60.

With reference to FIGS. 2, 5, and 6, the housing 50 has a plurality of upright inner support members 66 extending peripherally around the opening 64. As shown, the support members 66 have an inner outwardly directed flange 68 defining an outer recess 70 at an outer surface of the support members 66. Also, the support members 66 are spaced from each other to define apertures 67 between the support members 66. The housing 50 has a plurality of upright outer support members 72 which extend peripherally around the inner support members 66, with the inner and outer support members 66 and 72 defining a groove 74 intermediate the inner and outer support members 66 and 72. As shown, the outer support members 72 have an outwardly directed flange 76 defining an inner recess 78 on the inner surface of the outer support members 72. Also, the outer support members 72 are spaced from each other to define apertures 73 between the support members 72.

The housing cap 56 comprises a relatively thin ring 80 defining a central aperture 82 which extends through the cap 56. The cap 56 has an inwardly directed flange 84 extending peripherally around the aperture 82 adjacent the aperture 82. The cap 56 also has an inwardly directed flange 86 extending peripherally around the ring 80 adjacent an outer edge of the ring 80 and defining an outer recess 88 at the outer edge of the ring 80. The housing 50 including the cap 56 may be constructed from any suitable plastic material.

The filter 52 is pervious to passage of air but substantially impervious to the passage of bacteria. The filter 52 may be constructed from any suitable material, such as sintered polyethylene. As shown, the filter 52 has the general shape of a cylinder 90 defining a central bore 92 extending through the cylinder 90. Also, the filter 52 has a pair of opposed inner recesses 94 for a purpose which will be described below.

The valve element 54 may be constructed from any suitable elastic material, such as rubber. As shown, the valve element 54 has a generally circular diaphragm 96, with a two-sided rim 98 extending peripherally around the diaphragm 96 at the outer edge of the diaphragm 96. The valve element 54 also has an inner plug 100 extending from a central portion of the diaphragm 96 on an inner surface of the diaphragm 96. The plug 100 has a generally rectangular cross-section in the shape of the opening 64 of the housing 50. The plug 100 has a plurality of channels 102 extending along sides of the plug 100, with the plug 100 having beads 104 at the inner end of the plug 100 which close inner ends of the channels 102, such that the channels 102 extend from the beads 104 to the diaphragm 96.

During assembly of the vent 16, the valve element 54 is positioned on the housing 50 with an inner end of the plug 100 received in the housing opening 64, and with the inner side of the valve element rim 98 positioned in the recesses 70 of the inner support members 66, such that the valve element rim 98 makes sealing engagement with the inner support members 66. As shown, the inner end of the plug 100 has an arcuate shape to conform with the contour of the lumen 62. Next, the filter 52 is positioned in the housing groove 74 with the filter recesses 94 receiving opposed ends of the conduit section 60 in the groove 74. Finally, the cap 56 is positioned on the assembly with the flange 84 of the cap 56 being received inside the outer portion of the valve element rim 98, such that the cap flange 84 makes sealing engagement with the valve element 54. Also, the cap flange 86 is received in the recesses 78 of the outer support members 72, and the flanges 76 of the outer support members 72 are received in the recess 88 of the cap 56. The flange 86 of the cap 56 and the flanges 76 of the outer support members 72 may be secured together by suitable adhesive in order to secure the cap 56 in place on the outer support members 72 and retain the vent assembly together. In the assembled configuration of the vent 16, the diaphragm 96 of the valve element 54 closes the vent 16 to the atmosphere on the inside of the inner support members 66, while the cap 56 closes the vent 16 to the atmosphere intermediate the inner support members 66 and the outer support members 72, with the valve element 54 making sealing engagement with the cap 56 to prevent the passage of air between the cap 56 and the valve element 54. Thus, the cap 56 and valve element diaphragm 96 define a chamber in the housing 50, with the filter 52 communicating with the valve element plug 100 between the apertures 67, and with the filter 52 communicating with the atmosphere through the apertures 73.

With reference to FIGS. 5 and 6, in the normal position of the valve element 54, the diaphragm 96 maintains the plug 100 in a first outer position with the beads 104 located in the opening 64 of the conduit section 64. In this configuration, the faces of the plug 100 and the beads 104 sealingly engage against the conduit section 60 in the opening 64 to prevent communication between the plug channels 102 and the lumen 62 in the conduit section 60. Thus, in the first outer position of the valve element 54, the valve is closed to prevent passage of fluid between the lumen 62 and the filter 52. In this manner, the valve element 54 normally prevents passage of liquid through the opening 64, and thus prevents contact of liquid against the filter 52 from the lumen 62 which otherwise might degrade and close the filter 52 and render the vent inoperable.

With reference to FIGS. 3 and 4, the valve element 54 may be pressed by the user in the region of the plug 100 through the aperture 82 of the cap 56 in order to place the plug 100 at a second inner position with the beads 104 located in the lumen 62 of the conduit section 60. In this configuration, communication is established between the plug channels 102 and the lumen 62 of the conduit section 60. Thus, at the inner position of the plug 100, air is permitted to pass from the atmosphere through the apertures 73, the filter 52, the apertures 67, and through the plug channels 102 and opening 64 into the lumen 62 of the conduit section 60, with the filter 52 removing bacteria from the air which passes from the atmosphere into the lumen 62. In this manner, the lumen 62 of the conduit section 60 and the lumen 38 of the drainage tube 14 may be vented by passage of air from the atmosphere into the lumens while the filter 52 removes bacteria from the air. Thus, when columns of urine collect in the lumen 38 of the drainage tube 14, the valve element 54 of the vent 16 may be pressed in order to vent the lumen 38 and alleviate the negative pressure in the drainage tube lumen 38, such that the urine columns rapidly drain through the drainage tube 14 into the collection bag 18. When the valve element 54 is then released after liquid drainage, the plug 100 again assumes its outer sealing position, as shown in FIGS. 5 and 6, in order to close the opening 64 of the conduit section 60 and prevent passage of fluid through the opening 64.

Thus, in accordance with the present invention, when columns of urine collect in the drainage tube 14, the valve element 54 may be readily depressed in order to vent the drainage tube 14 and alleviate negative pressure in the drainage tube 14. After the venting procedure has been completed, the valve element 54 is released, and the plug 100 of the valve element 54 assumes its sealing position to prevent passage of urine through the opening 64 of the conduit section 60 against the filter 52, thus preventing degradation of the filter 52.

The foregoing detailed description is given for clearness of understanding only, and no unnecessary limitations should be understood therefrom, as modifications will be obvious to those skilled in the art.

I claim:

1. Vent means in a urine drainage system, comprising:
a conduit having a lumen for drainage of urine and an opening in a wall of the conduit communicating with said lumen;
a housing defining passageway means communicating with said opening;
a plug received in the opening inside said housing, said plug being movable between a first outer closed position with the plug sealingly engaged in said opening and closing the opening to prevent passage of urine through the opening, and a second inner open position with the plug permitting passage of air through the opening between the passageway means and the lumen;
a filter in the housing pervious to air and substantially impervious to the passage of bacteria, said filter closing said passageway means to the atmosphere to filter air passing from the atmosphere to the passageway means, said housing having a conduit section defining a portion of said conduit containing said opening.

2. The vent means of claim 1 wherein said plug is constructed from an elastic material.

3. The vent means of claim 1 wherein said plug includes channel means in a side of the plug, and bead means closing said channel means at an inner end of the plug, such that said bead means sealingly engages in said opening at said first plug position to prevent communication between the lumen and said channel means, and said channel means communicates with the lumen at said second plug position to permit passage of air between the passageway means and the lumen through the channel means.

4. The vent means of claim 1 wherein said filter extends peripherally around the opening in said housing, with said vent means being closed to the atmosphere at an outer portion of the filter over the opening.

5. The vent means of claim 1 including a flexible diaphragm extending outwardly from an outer end of the plug peripherally around the plug, said housing having upright support means located peripherally around the opening to engage and support an outer edge of the diaphragm with the support means sealingly engaging against the diaphragm, said support means defining aperture means to permit passage of air therethrough.

6. The vent means of claim 5 wherein said filter comprises an annular ring extending peripherally around the support means.

7. The vent means of claim 6 wherein said housing includes a cap covering said filter and engaging against an outer edge of the diaphragm on an outer surface of the diaphragm, said cap having a central aperture located above said plug.

8. The vent means of claim 7 wherein said housing includes outer upright support means located peripherally around the filter to support an outer edge of said cap, said outer support means defining opening means to permit passage of air therethrough.

9. Vent means for a liquid drainage system, comprising:
a conduit having a lumen;
a housing having a conduit section defining a lumen, said conduit section being attached to said conduit with the lumen of the conduit section communicating with the lumen of the conduit, said conduit section having an opening extending therethrough and communicating with the lumen of the conduit section, said housing having at least one upright support member extending peripherally around the opening, with said support member defining aperture means extending through the support member;
an elastic valve member having a generally circular diaphragm with an outer edge of the diaphragm being connected to an outer edge of the support member with the diaphragm closing said opening to the atmosphere inside said support member, said valve member having a plug extending inwardly from a central portion of the diaphragm and being received in said opening, said plug having a plurality of channels on a side of the plug and a plurality of beads closing an inner end of said channels, said plug normally being positioned in said opening with said beads sealingly engaging against said opening to prevent communication between the lumen of the conduit section and the plug channels, and said plug being movable to an inner position with the beads located in the lumen of the conduit section and with the plug channels communicating with the lumen of the conduit section to permit passage of air through the opening between the housing aperture means and the lumen of the conduit section;
a filter in the housing pervious to air and substantially impervious to the passage of bacteria, said filter having the general shape of a cylinder and surrounding the support member, said housing having a cap with an inner edge of the cap engaging against an outer edge of the diaphragm on an outer surface of the diaphragm, said cap closing an outer edge of the filter to the atmosphere and having a central aperture located above said plug, said filter having a pair of opposed inner recesses to receive spaced portions of said conduit section.

10. Vent means for a liquid drainage system, comprising:

a conduit having a lumen;

a housing having a conduit section defining a lumen, said conduit section being attached to said conduit with the lumen of the conduit section communicating with the lumen of the conduit, said conduit section having an opening extending therethrough and communicating with the lumen of the conduit section, said housing having at least one upright support member extending peripherally around the opening, with said support member defining aperture means extending through the support member;

an elastic valve member having a generally circular diaphragm with an outer edge of the diaphragm being connected to an outer edge of the support member with the diaphgram closing said opening to the atmosphere inside said support member, said valve member having a plug extending inwardly from a central portion of the diaphragm and being received in said opening, said plug having a plurality of channels on a side of the plug and a plurality of beads closing an inner end of said channels, said plug normally being positioned in said opening with said beads sealingly engaging against said opening to prevent communication between the lumen of the conduit section and the plug channels, and said plug being movable to an inner position with the beads located in the lumen of the conduit section and with the plug channels communicating with the lumen of the conduit section to permit passage of air through the opening between the housing aperture means and the lumen of the conduit section;

a filter in the housing pervious to air and substantially impervious to the passage of bacteria, said filter having the general shape of a cylinder and surrounding the support member, said housing having a cap with an inner edge of the cap engaging against an outer edge of the diaphragm on an outer surface of the diaphragm, said cap closing an outer edge of the filter to the atmosphere and having a central aperture located above said plug, said housing including at least one upright outer support member extending peripherally around the filter, with an outer edge of the outer support member being connected to an outer edge of the cap, said outer support member having aperture means permitting communication between the atmosphere and said filter.

* * * * *